US012637439B2

(12) United States Patent
Marlowe

(10) Patent No.: US 12,637,439 B2
(45) Date of Patent: May 26, 2026

(54) PREPARATION OF CANNABICHROMENE AND RELATED CANNABINOIDS

(71) Applicant: BayMedica, Inc., Incline Village, NV (US)

(72) Inventor: Charles K. Marlowe, Incline Village, CA (US)

(73) Assignee: BayMedica, Inc., Incline Village, NV (US)

( * ) Notice: Subject to any disclaimer, the term of this patent is extended or adjusted under 35 U.S.C. 154(b) by 426 days.

(21) Appl. No.: 17/788,716

(22) PCT Filed: Dec. 23, 2020

(86) PCT No.: PCT/US2020/066965
§ 371 (c)(1),
(2) Date: Jun. 23, 2022

(87) PCT Pub. No.: WO2021/133989
PCT Pub. Date: Jul. 1, 2021

(65) Prior Publication Data

US 2023/0063862 A1 Mar. 2, 2023

Related U.S. Application Data

(60) Provisional application No. 62/954,287, filed on Dec. 27, 2019.

(51) Int. Cl.
*C07D 311/80* (2006.01)
*C07D 311/58* (2006.01)

(52) U.S. Cl.
CPC .......... *C07D 311/80* (2013.01); *C07D 311/58* (2013.01)

(58) Field of Classification Search
CPC .................................................... C07D 311/80
See application file for complete search history.

(56) References Cited

U.S. PATENT DOCUMENTS

| | | | |
|---|---|---|---|
| 3,919,322 | A | 11/1975 | Brossi et al. |
| 4,315,862 | A | 2/1982 | Elsohly et al. |
| 5,919,651 | A | 7/1999 | Hitzeman et al. |
| 6,033,883 | A | 3/2000 | Barr et al. |
| 6,228,647 | B1 | 5/2001 | Voytas et al. |
| 6,258,566 | B1 | 7/2001 | Barr et al. |
| 7,078,233 | B2 | 7/2006 | Barr et al. |
| 8,124,390 | B2 | 2/2012 | Kuzuyama et al. |
| 8,236,552 | B2 | 8/2012 | Millis et al. |
| 8,884,100 | B2 | 11/2014 | Page et al. |
| 9,376,367 | B2 | 6/2016 | Herkenroth et al. |
| 9,546,362 | B2 | 1/2017 | Page et al. |
| 9,611,460 | B2 | 4/2017 | Page et al. |
| 9,637,763 | B2 | 5/2017 | Barr |
| 10,837,031 | B2 | 11/2020 | Barr et al. |
| 11,399,611 | B2 | 8/2022 | Philippe et al. |
| 11,414,366 | B2 | 8/2022 | Nandy et al. |
| 2003/0158191 | A1 | 8/2003 | Travis |
| 2003/0232101 | A1 | 12/2003 | Travis |
| 2008/0031977 | A1 | 2/2008 | Musty et al. |
| 2008/0275135 | A1 | 11/2008 | Mechoulam et al. |
| 2010/0298579 | A1 | 11/2010 | Steup et al. |
| 2014/0141476 | A1 | 5/2014 | Page et al. |
| 2015/0299732 | A1 | 10/2015 | Millis et al. |
| 2015/0336874 | A1 | 11/2015 | Koch et al. |
| 2016/0010126 | A1 | 1/2016 | Poulos et al. |
| 2016/0053220 | A1 | 2/2016 | Peet et al. |
| 2016/0068869 | A1 | 3/2016 | Piotrowski et al. |
| 2018/0263952 | A1 | 9/2018 | Biro et al. |
| 2018/0334692 | A1 | 11/2018 | Barr et al. |
| 2021/0040512 | A1 | 2/2021 | Barr et al. |
| 2021/0403408 | A1 | 12/2021 | Barr et al. |
| 2022/0177858 | A1 | 6/2022 | Noble et al. |

FOREIGN PATENT DOCUMENTS

| | | | |
|---|---|---|---|
| EP | 0304842 | A2 | 3/1989 |
| EP | 3666765 | A1 | 6/2020 |
| WO | 2020214574 | A1 | 10/2010 |
| WO | 2020214951 | A1 | 10/2010 |
| WO | 2014177593 | A1 | 11/2014 |
| WO | 2017051020 | A1 | 3/2017 |
| WO | 2017161041 | A1 | 9/2017 |
| WO | 2017/175064 | A1 | 10/2017 |
| WO | 2018057385 | A2 | 3/2018 |
| WO | 2018148848 | A1 | 8/2018 |
| WO | 2018200888 | A1 | 11/2018 |
| WO | 2019071000 | A1 | 4/2019 |

OTHER PUBLICATIONS

International Search Report and Written Opinion, dated Mar. 15, 2021, PCT Application No. PCT/US20/66965, 7 pages.

Lee, et al., "Concise Synthesis of Biologically Interesting (+/−)Cannabichromene, (+/−)-Cannabichromenic Acid, and (+/−)-Daurichromenic Acid" Bulletin of the Korean Chemical Society, 2005, vol. 26, pp. 1933-1936.

Caprioglio et al., "One-Pot Total Synthesis of Cannabinol via Iodine-Mediated Deconstructive Annulation," Organic Letters, 2019, vol. 21, pp. 6122-6125.

Abdulkhani et al., "Evaluation of the Antibacterial Activity of Cellulose Nanofibers/Polylactic Acid Composites Coated With Ethanolic Extract of Propolis", Polymer Composites, vol. 38(1), pp. 13-19 (2017).

Baek SH et al. (1985) "Boron trifluoride etherate on alumina—a modified Lewis acid reagent. An improved synthesis of cannabinol." Tetrahedron Letters 26(8): 1083-1086.

(Continued)

*Primary Examiner* — Golam M Shameem
(74) *Attorney, Agent, or Firm* — Michael J. Adams

(57) ABSTRACT

Methods for the production of cannabichromene and related cannabinoid compounds are disclosed. The methods include: forming a reaction mixture comprising 3,7-dimethylocta-2,6-dienal, a diamine, and olivetol or a related starting material; and maintaining the reaction mixture under conditions sufficient to form the desired product. Methods of the present disclosure may also include one-pot conversion of cannabichromene-type products to cannabinol-type products.

31 Claims, 2 Drawing Sheets

(56) References Cited

OTHER PUBLICATIONS

Black PN, et al. (May 16, 2006) "Yeast acyl-CoA synthetases at the crossroads of fatty acid metabolism and regulation." Biochim Biophys Acta. 1771(3):286-98.
Crombie L, et al. (Jan. 1, 1988) "Synthesis of Cannabinoids Carrying ω-Carboxy Substituents: The Cannabidiols, Cannabinol and Δ1- and Δ6-Tetrahydrocannabinols of this Series." J. Chem. Soc. Perkin Trans. I 1998: 1255-1262.
Driessen, Robert Andre, "Deuterium Labeled Gannabinoids: synthesis and mass spectrometry Proefschrift Ter Verkrijging Van De Graad Van Doctor in De Wiskunde En Natuurwetenschappen Aan De Rijksuniversiteit TE Utrecht, OP Gezag Van De Rector Magnificus Prof. Dr. A. Verhoeff, Volgens Beslutt Van Het College Van Decanen in H", Utrecht, pp. 1-146 (1979).
Elsohly et al., "Synthesis and Antimicrobial Activities of Certain Cannabichromene and Cannabigerol Related Compounds", J. Pharmaceutical Sciences, vol. 71, No. 12 (1982).
Elsohly, M et al., (2005) "Chemical constituents of marijuana: The complex mixture of natural cannabinoids." Life Sciences 78: 539-548.
Fellermeier M, et al. (May 8, 1998) "Prenylation of olivetolate by a hemp transferase yields cannabigerolic acid, the precursor of tetrahydrocannabinol." FEBS Lett 427: 283-285.
Flores-Sanchez I, et al. (Apr. 8, 2008) "Secondary metabolism in cannabis." Phytochem Rev 7:615-639.
Flores-Sanchez I (Oct. 29, 2008) "Polyketide synthases in Cannabis sativa L." Doctoral thesis, Leiden University.
Flores-Sanchez I, et al. (Dec. 3, 2008) "PKS Activities and Biosynthesis of Cannabinoids and Flavonoids in Cannabis sativa L. Plants." Plant Cell Physiol. 49(12): 1767-1782.
Gagne S et al. (Jul. 31, 2012) "Identification of olivetolic acid cyclase from Cannabis sativa reveals a unique catalytic route to plant polyketides." Proc. Nat. Acad. Sci. USA 109: 12811-12816.
Ghoudhary et al., "Isolation and charaterization of phenolic compound from Rhodiola imbricata, a Trans- Himalayan food crop having antioxidant and anticancer potential", J. of Functional Foods, vol. 16, pp. 183-193 (2015).
Girard et al., "A simple and eficient synthesis of 5'-(2H3)olivetol", Can. J. Chem. vol. 65, pp. 189-190 (1987).
Harvey, D. J. and Brown, N. K., "Comparative In Vitro Metabolism of the Cannabinoids", Pharmacology, Biochemistry and Behavior, vol. 40, pp. 533-540 (1991).
Hazekamp A et al., "Chromatographic and Spectroscopic Data of Cannabinoids from Cannabis sativa L." Journal of Liquid Chromatography & Related Techniques 28: 2361-2382 (2005).
Hwangbo et al., "Inhibition of DNA Topoisomerases I and II of Compounds from Renoutria japonica", Archives of Pharmacal Research, vol. 35(9), pp. 1583-1589 (2012).
Kumano T et al., "Chemoenzymatic syntheses of prenylated aromatic small molecules using Streptomyces prenyltransferases with relaxed substrate specificities." Bioorg Med Chem. 16(17): 8117-8126 (2008).
Kuzuyama T, et al., "Structural basis for the promiscuous biosynthetic prenylation of aromatic natural products." Nature 435(7044): 983-987 (2005).
Lee Y R et al., "Efficient and general method for the synthesis of benzopyrans by ethylenediamine diacetate- catalyzed reactions of resorcinols with alfa, beta-unsaturated aldehydes. One step synthesis of biologically active (+/-)-confluentin and (+/-)-daurichromenic acid", Tetrahedron Letters, Elsevier, Amsterdam, NL, vol. 46, No. 44, pp. 7539-7543 (2005).
Li, M. et al. (Sep. 4, 2015) "De novo production of resveratrol from glucose or ethanol by engineered Saccharomyces cerevisiae." Metabolic Engineering 32 (2015) 1-11.
Mechoulam R, et al., "Stereoselective synthesis of cannabinoid 1,5 dienes." Tetrahedron Letters 60:5349-5352 (1969).
Miyazawa T, et al. (Sep. 16, 2015) "Identification of Middle Chain Fatty Acyl-CoA Ligase Responsible for the Biosynthesis of 2-Alkylmalonyl-CoAs for Polyketide Extender Unit." J. Biol. Chem. 290: 26994-27011.
Morimoto S, et al. (Nov. 20, 1998) "Purification and characterization of cannabichromenic acid synthase from Cannabis sativa." Phytochemistry 49: 1525-1529.
Morimoto S, et al. (1999) "Biosynthesis of cannabinoids in Cannabis sativa L." Curr Top Phytochem 2: 103-113.
Pamplaniyil, K., "Identification, isolation and functional characterization of prenyltransferases in Cannabis sativa L.", Jan. 1, 2018; Technischen Universität Dortmund; PhD dissertation; https://eldorado.tu-dortmund.de/handle/2003/36335; 141 pages.
Pitt C. G et al., "The synthesis of deuterium, carbon-14, and carrier-free tritium labeled cannabinoids", Journal of Labelled Compounds., GB, vol. 11, No. 4, pp. 551-575, (1975).
PubChem Compound Summary, PubChem CID: 66591394, Jan. 31, 2020, pp. 1-11, retrieved from the Internet (pubchem.ncbi.nlm.nih.gov/compound/66591394, p. 2, formula).
Qi et al., "$\Delta^9$—Tetrahydrocannabinol Immunochemical Studies: Haptens, Monoclonal Antibodies, and a Convenient Synthesis of Radiolabeled $\Delta^9$—Tetrahydrocannabinol", Journal of Medicinal Chemistry, US, vol. 48, No. 23, pp. 7389-7399 (2005).
Roth et al. "Regioselective synthesis of isotopically labeled 49-tetrahydrocannabinolic acid A (THCA-A-D3) by reaction of 49-tetrahydrocannabinol-D3 with magnesium methyl carbonate", Forensic Science International 222, Issue 1-3, pp. 368-372 (2012).
Russo, B. & MARCU, Johan "Chapter Three, Cannabis Pharmacology: The Usual Suspects and a Few Promising Leads", Advances in Pharmacology, vol. 80, pp. 67-134 (2017).
Shockey J, et al. (Jun. 2003) "Arabadopsis Contains a Large Superfamily of Acyl-Activating Enzymes. Phylogenetic and Biochemical Analysis Reveals a New Class of Acyl-Coenzyme A Synthetases." Plant Physiology 132: 1065-1076.
Shoyama Y, et al. (1978) "Cannabis XI. Synthesis of cannabigerorcinic-carboxyl-14C acid, cannabigerovarinic carboxyl-14C acid, cannabidivarinic-carboxyl-14C acid and dl-cannabichromevarinic-carboxyl-14C acid." Journal of Labelled Compounds and Radiopharmaceuticals. 14(8): 835-842.
Sirikantaramas S, et al. (2017) "Chapter 8. Cannabinoids: Biosynthesis and Biotechnological Applications." *Cannabis sativa L.*—Botany and Biotechnology, S. Chandra et al. (eds.), Springer International Publishing AG, pp. 183-206.
Stout JM et al. (Jun. 1, 2012) "The hexanoyl-CoA precursor for cannabinoid biosynthesis is formed by an acyl-activating enzyme in Cannabis sativa trichomes." The Plant Journal 71:353-365.
Taura et al., "Purification and Characterization of Cannabidiolic-acid Synthase from *Cannabis Sativa L.*", Journal of Biological Chemistry, vol. 271, No. 29, Jul. 19, 1996, pp. 17411-17416.
Taura F, et al. (Jun. 26, 2007) "Cannabidiolic-acid synthase, the chemotype-determining enzyme in the fiber-type *Cannabis sativa*." FEBS Lett 581: 2929-2934.
Taura F, et al. (Jun. 18, 2009) "Characterization of olivetol synthase, a polyketide synthase putatively involved in cannabinoid biosynthetic pathway." FEBS Lett 583: 2061-2066.
Taylor, Edward C. and Strojny, E.J., "The Synthesis of Some Model Compounds Related to Tetrahydrocannabinol", Journal of the American Chemical Society, vol. 82, pp. 5198-5202 (1960).
Van Bakel H et al. (Oct. 20, 2011) "The draft genome and transcriptome of Cannabis sativa." Genome Biology 12: R102.
Yang X, et al. (Jan. 18, 2016) "Structural basis for olivetolic acid formation by a polyketide cyclase from Cannabis sativa." Febs J. 283:1088-1106.
Yun et al. "UPLC-Q-TOF/MS characterization, HPLC fingerprint analysis and species differentiation for quality control of Nigella glandulifera Freyn et Sint seeds and *Nigella sativa L.* seeds", Analytical Methods, 6(13), pp. 4845-4852 (2014).
Zanato et al., "Synthesis, radio-synthesis and in vitro evaluation of terminally fluorinated derivatives of HU-210 and HU-211 as novel candidate PET tracers", ORGANIC & Biomolecular Chemistry, vol. 15, No. 9, pp. 2086-2096 (2017).
130414-07-2, STN Registry, published on Nov. 16, 1990.
134914-55-9, STN Registry, published on Jul. 19, 1991.

PREPARATION OF CANNABICHROMENE AND RELATED CANNABINOIDS

CROSS-REFERENCE TO RELATED APPLICATIONS

The present application claims priority to U.S. Provisional Pat. Appl. No. 62/954,287, filed on Dec. 27, 2019, which application is incorporated herein by reference in its entirety.

BACKGROUND OF THE INVENTION

*Cannabis sativa* varieties have been cultivated and utilized extensively throughout the world for a number of applications. Stems, branches, and leaves are used in fibers and fiber-based products; sprouts and seeds as food; seeds for inexpensive oils; flowers for aromatic, recreational, ritual and medicinal purposes; and flowers and roots for nutritional and additional medicinal and pharmaceutical applications. Indeed, many controlled clinical studies and anecdotal or open-label studies in humans have been documented that demonstrate beneficial effects of both plant extracts and purified *C. sativa* plant compounds in many human medical conditions. Beneficial activities of the cannabinoid family of compounds described from human studies range from neurological to mood/behavior disorders, and to gastrointestinal disorders as well as sleeping, appetite and fatigue problems. Other uses or potential uses include the treatment of various microbial and viral infections and the treatment of a number of cancers.

BRIEF SUMMARY OF THE INVENTION

Provided herein are methods for preparing cannabichromene-type compounds according to Formula I:

(I)

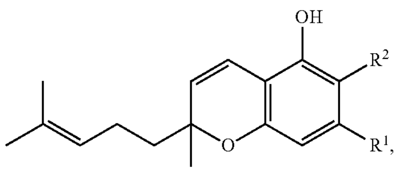

and salts thereof. The methods include:

forming a reaction mixture comprising 3,7-dimethylocta-2,6-dienal, a diamine, and a compound of Formula II:

(II)

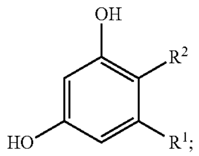

and maintaining the reaction mixture under conditions sufficient to form the compound of Formula I.

In some embodiments, the compound of Formula II is olivetol and the compound of Formula I is cannabichromene. In some embodiments, the diamine is N,N'-dimethylethylene-diamine.

In some embodiments, the methods further include converting (e.g., in a one pot reaction) the cannabichromene-type compound of Formula I to a cannabinol-type compound of Formula III:

(III)

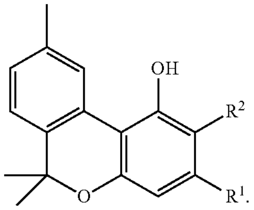

Exemplary embodiments provided in accordance with the presently disclosed subject matter include, but are not limited to, the claims and the following embodiments:

1. A method for preparing a compound according to Formula I:

(I)

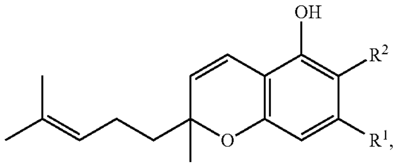

or a salt thereof, the method comprising:

forming a reaction mixture comprising 3,7-dimethylocta-2,6-dienal, a diamine, and a compound of Formula II:

(II)

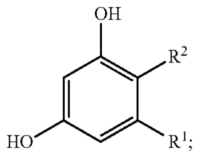

and maintaining the reaction mixture under conditions sufficient to form the compound of Formula I; wherein:

$R^1$ is selected from the group consisting of $C_1$-$C_{20}$ alkyl, $C_1$-$C_{20}$ haloalkyl, $C_1$-$C_{20}$ hydroxyalkyl, deuterated $C_1$-$C_2$ alkyl, tritiated $C_1$-$C_{20}$ alkyl, and $C_2$-$C_{20}$ alkenyl;

$R^2$ is selected from the group consisting of H and —$COOR^{2a}$; and $R^{2a}$ is selected from the group consisting of H and $C_1$-$C_6$ alkyl.

2. The method of embodiment 1, wherein the diamine is selected from the group consisting of N,N'-dimethylethylenediamine; N,N-dimethylethylenediamine; N,N-diethylethylenediamine; N,N'-diphenylethylenediamine; N,N'-dibenzylethylenediamine; N,N'-bis(2-hydroxyethyl) ethylenediamine; N,N'-dimethylpropylenediamine; N,N-dimethylpropylenediamine; N,N-diethylpropylenediamine; N,N'-diphenylpropylenediamine; N,N'-dibenzylpropylenediamine; N,N'-bis(2-hydroxyethyl)propylenediamine; 1,2-diaminocyclohexane; N,N'-dimethyl-1,2-diaminocyclohexane; and 1,2-cyclopentanediamine.

3. The method of embodiment 1 or embodiment 2, wherein the reaction mixture contains about 1.1-10 molar equivalents of the 3,7-dimethylocta-2,6-dienal with respect to the compound of Formula II.

4. The method of embodiment 3, wherein the reaction mixture containing about 1.1-2 molar equivalents of the 3,7-dimethylocta-2,6-dienal with respect to the compound of Formula II.

5. The method of any one of embodiments 1-4, wherein the reaction mixture contains about 0.01-10 molar equivalents of the diamine with respect to the compound of Formula II.

6. The method of embodiment 5, wherein the reaction mixture contains about 0.25 molar equivalents of the diamine with respect to the compound of Formula II.

7. The method of any one of embodiments 1-6, wherein the reaction mixture is maintained at a reaction temperature ranging from about 20° C. to about 70° C.

8. The method embodiment 7, wherein the reaction mixture is maintained at the reaction temperature for a period of time ranging from about 30 minutes to about 24 hours.

9. The method of any one of embodiments 1-8, wherein the reaction mixture further comprises a solvent.

10. The method of embodiment 9, wherein the solvent is selected from the group consisting of toluene, chloroform, methylene chloride, dichloroethane, ethyl acetate, acetonitrile, acetone, tetrahydrofuran, benzene, ethylbenzene, xylenes, diethyl ether, dimethyl formamide, dimethyl sulfoxide, petroleum ether, and mixtures thereof.

11. The method of embodiment 9, wherein the solvent is selected from the group consisting of toluene, chloroform, isopropanol, and mixtures thereof.

12. The method of any one of embodiments 1-11, wherein the 3,7-dimethylocta-2,6-dienal comprises neral, geranial, or a combination thereof.

13. The method of any one of embodiments 1-11, wherein the 3,7-dimethylocta-2,6-dienal comprises E,Z-citral.

14. The method of any one of embodiments 1-13, wherein $R^2$ is H.

15. The method of any one of embodiments 1-13, wherein $R^2$ is —COOH.

16. The method of any one of embodiments 1-15, wherein $R^1$ is n-pentyl.

17. The method of any one of embodiments 1-16, wherein the compound of Formula II is purified or semi-purified.

18. The method of any one of embodiments 1-17, further comprising converting the compound of Formula I to a compound of Formula III:

(III)

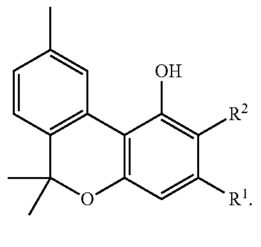

19. The method of embodiment 18, wherein the converting comprises combining the compound of Formula I with an iodine source and an oxidizing agent.

20. The method of embodiment 19, wherein the iodine source is selected from the group consisting of sodium iodide, lithium iodide, potassium iodide, magnesium iodide, calcium iodide, ammonium iodide, aluminum iodide, zinc iodide, barium iodide, cesium iodide, N-iodosuccinimide, and combinations thereof.

21. The method of embodiment 18, wherein the converting comprises combining the compound of Formula I with an oxidizing agent.

22. The method of any one of embodiments 19-21, wherein the oxidizing agent is selected from the group consisting of potassium peroxymonosulfate, a peroxide, 2-iodoxybenzoic acid, sodium hypochlorite, and combinations thereof.

23. The method of embodiment 18, wherein the converting comprises combining the compound of Formula I with sodium iodide and potassium peroxymonosulfate.

24. The method of embodiment 18, wherein the converting comprises combining the compound of Formula I with elemental sulfur.

25. The method of embodiment 18, wherein the converting comprises combining the compound of Formula I with a metal dehydrogenation catalyst.

26. The method of embodiment 25, wherein the metal dehydrogenation catalyst comprises palladium on carbon, platinum on carbon, palladium on alumina, or platinum on alumina.

27. The method of any one of embodiments 18-27, wherein the converting further comprises combining the compound of Formula I with an acid.

28. The method of embodiment 27, wherein the acid is p-toluenesulfonic acid.

29. The method of any one of embodiments 18-28, wherein the step of converting the compound of Formula I to a compound of Formula III is conducted as a one-pot reaction in the reaction mixture for forming the compound of Formula I.

DETAILED DESCRIPTION OF THE INVENTION

Figure 1A:
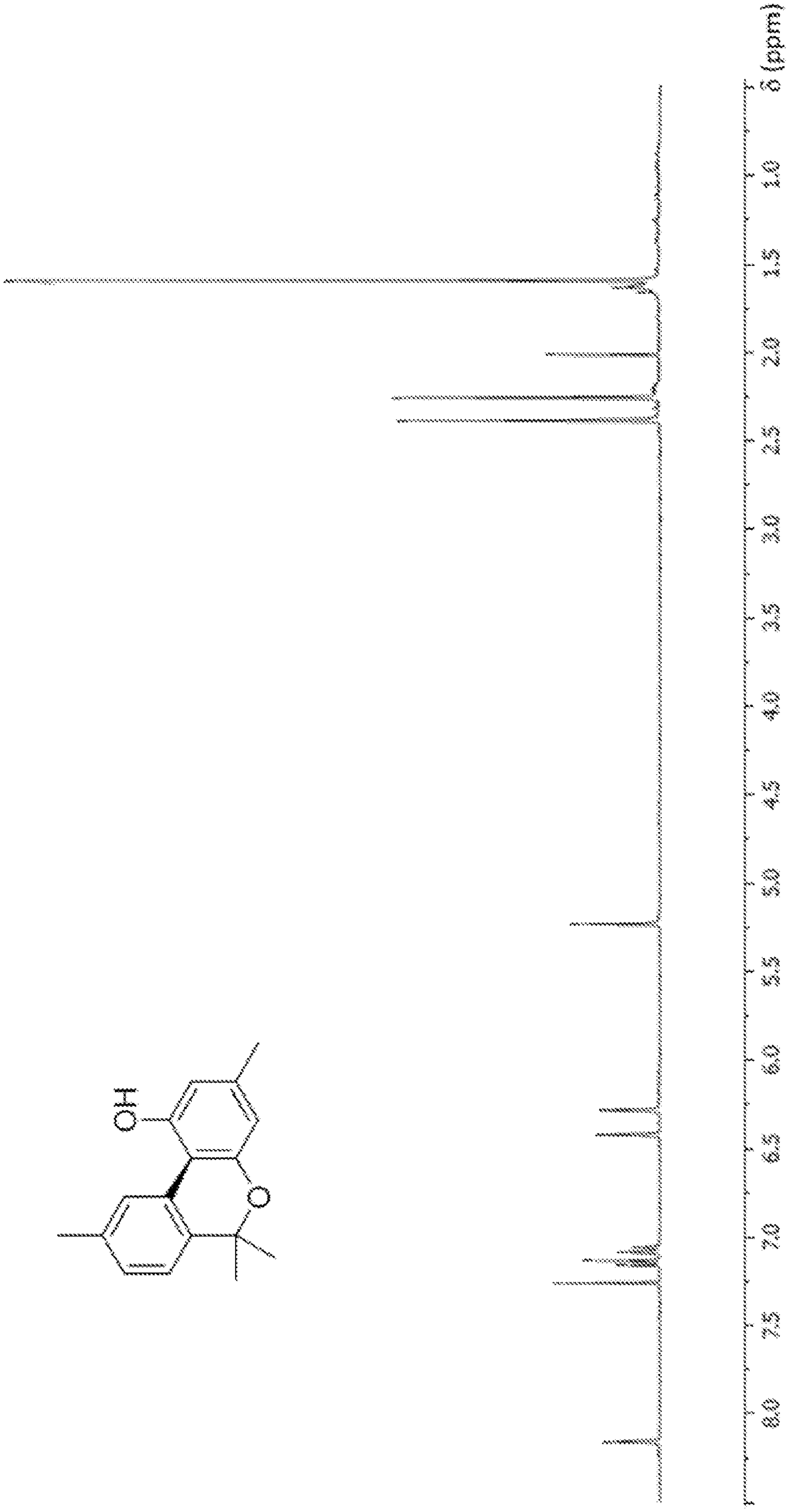
FIG. 1A shows a proton NMR spectrum recorded for 3,6,6,9-tetramethyl-6H-benzo[c]chromen-1-ol.
Figure 1B:
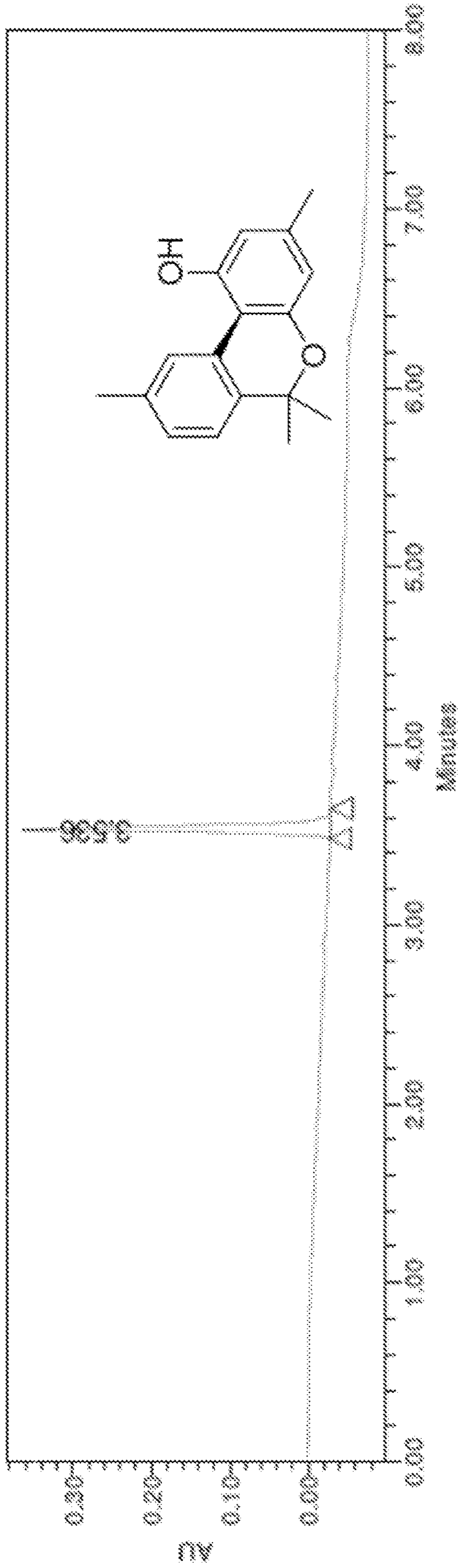
FIG. 1B shows a reverse-phase chromatogram recorded for 3,6,6,9-tetramethyl-6H-benzo[c]chromen-1-ol.

Provided herein are rapid and high-yielding methods for the preparation of cannabichromene, cannabinol, and related cannabinoids. The methods can be used to produce valuable cannabinoids on kilogram-scale and be conducted via convenient one-pot procedures. As described herein, diamine catalysts have been found particularly advantageous for forming cannabichromene-type products.

I. Definitions

The term "cannabichromene" refers to 2-methyl-2-(4-methyl-3-penten-1-yl)-7-pentyl-2H-1-benzopyran-5-ol (CAS Registry No. 20675-51-8). "Cannabichromene analogs" include, but are not limited to, compounds wherein a $C_1$-$C_4$ alkyl group, a branched $C_5$ alkyl group, a $C_6$-$C_{20}$ alkyl group, a $C_1$-$C_{20}$ haloalkyl group, a $C_1$-$C_{20}$ hydroxyalkyl group, a deuterated $C_1$-$C_{20}$ alkyl group, a tritiated $C_1$-$C_{20}$ alkyl group, or a $C_2$-$C_{20}$ alkenyl group is present where 7-pentyl is present in cannabichromene.

The term "cannabinol" refers to 6,6,9-trimethyl-3-pentyl-6H-dibenzo[b,d]pyran-1-ol (CAS Registry No. 521-35-7). "Cannabinol analogs" include, but are not limited to, compounds wherein a $C_1$-$C_4$ alkyl group, a branched $C_5$ alkyl group, a $C_6$-$C_{20}$ alkyl group, a $C_1$-$C_{20}$ haloalkyl group, a $C_1$-$C_{20}$ hydroxyalkyl group, a deuterated $C_1$-$C_{20}$ alkyl group, a tritiated $C_1$-$C_{20}$ alkyl group, or a $C_2$-$C_{20}$ alkenyl group is present where 3-pentyl is present in cannabinol.

The term “diamine” refers to a hydrocarbon compound having two amine substituents of the formula —$NR_2$, wherein each R group is independently selected from the group consisting of hydrogen, alkyl, hydroxyalkyl, aryl, arylalkyl, or acyl. Each amine substituent may independently be a primary amine, wherein both R groups are hydrogen; a secondary amine, wherein one R group is hydrogen and one R group is other than hydrogen; or a tertiary amine wherein both R groups are other than hydrogen.

As used herein, the term “iodine source” refers to an inorganic compound or an organic compound containing at least one iodine atom.

As used herein, the term “oxidizing” refers to the transfer of electron density from a substrate compound to an oxidizing agent. The electron density transfer typically occurs via a process including addition of oxygen to the substrate compound or removal of hydrogen from the substrate compound. The term “oxidizing agent” refers to a reagent that can accept electron density from the substrate compound.

The term “alkyl,” by itself or as part of another substituent, refers to a straight or branched, saturated, aliphatic radical. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_1$-6 alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

The term “alkenyl,” by itself or as part of another substituent, refers to an alkyl group, as defined herein, having one or more carbon-carbon double bonds. Examples of alkenyl groups include, but are not limited to, vinyl (i.e., ethenyl), crotyl (i.e., but-2-en-1-yl), penta-1,3-dien-1-yl, and the like. Alkenyl moieties may be further substituted, e.g., with aryl substituents (such as phenyl or hydroxyphenyl, in the case of 4-hydroxystyryl).

The terms “halogen” and “halo,” by themselves or as part of another substituent, refer to a fluorine, chlorine, bromine, or iodine atom.

The term “haloalkyl,” by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term “perfluoro” can be used to define a compound or radical where all the hydrogens are replaced with fluorine. For example, perfluoromethyl refers to 1,1,1-trifluoromethyl.

The term “hydroxyalkyl,” by itself or as part of another substituent, refers to an alkyl group where some or all of the hydrogen atoms are replaced with hydroxyl groups (i.e., —OH groups). As for alkyl and haloalkyl groups, hydroxyalkyl groups can have any suitable number of carbon atoms, such as $C_{1-6}$.

The term “deuterated” refers to a substituent (e.g., an alkyl group) having one or more deuterium atoms (i.e., $^2$H atoms) in place of one or more hydrogen atoms.

The term “tritiated” refers to a substituent (e.g., an alkyl group) having one or more tritium atoms (i.e., $^3$H atoms) in place of one or more hydrogen atoms.

The term “aryl” used alone or as part of a larger moiety as in “aralkyl,” “aralkoxy,” or “aryloxyalkyl,” refers to monocyclic or bicyclic ring systems having a total of five to fourteen ring members, wherein at least one ring in the system is aromatic and wherein each ring in the system contains 3 to 7 ring members. The term “aryl” may be used interchangeably with the term “aryl ring.” In certain embodiments of the present invention, “aryl” refers to an aromatic ring system which includes, but is not limited to, phenyl, biphenyl, naphthyl, anthracyl and the like, which may bear one or more substituents. Also included within the scope of the term “aryl,” as it is used herein, is a group in which an aromatic ring is fused to one or more non-aromatic rings, such as indanyl, phthalimidyl, naphthimidyl, phenanthridinyl, or tetrahydronaphthyl, and the like. The term “aryloxy” refers to a moiety—OR, wherein R is an aryl group as defined above.

As used herein, the terms “contacting” and “reacting” refer to the process of bringing into contact at least two distinct species such that they can react. It should be appreciated, however, that the resulting reaction product can be produced directly from a reaction between the added reagents or from an intermediate that can be produced from one or more of the added reagents in the reaction mixture.

As used herein, the term “converting” refers to reacting a starting material with at least one reagent to form an intermediate species or a product. The converting can also include reacting an intermediate with at least one reagent to form a further intermediate species or a product.

As used herein, the terms “about” and “around” indicate a close range around a numerical value when used to modify that specific value. If “X” were the value, for example, “about X” or “around X” would indicate a value from 0.9× to 1.1×, e.g., a value from 0.95× to 1.05×, or a value from 0.98× to 1.02×, or a value from 0.99× to 1.01×. Any reference to “about X” or “around X” specifically indicates at least the values X, 0.9×, 0.91×, 0.92×, 0.93×, 0.94×, 0.95×, 0.96×, 0.97×, 0.98×, 0.99×, 1.01×, 1.02×, 1.03×, 1.04×, 1.05×, 1.06×, 1.07×, 1.08×, 1.09×, and 1.1×, and values within this range II. Methods for Cannabinoid Synthesis Provided herein are methods for preparing cannabichromene-type compounds according to Formula I:

(I)

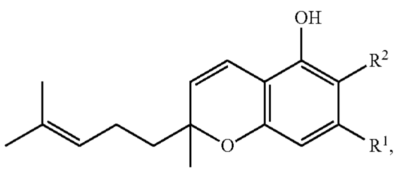

and salts thereof. The methods include:

forming a reaction mixture comprising 3,7-dimethylocta-2,6-dienal, a diamine, and a compound of Formula II:

(II)

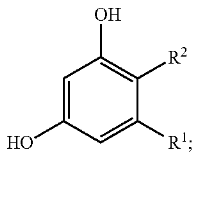

maintaining the reaction mixture under conditions sufficient to form the compound of Formula I; wherein:

$R^1$ is selected from the group consisting of $C_1$-$C_{20}$ alkyl, $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, and $C_2$-$C_{20}$ alkenyl;

$R^2$ is selected from the group consisting of H and —$COOR^{2a}$; and $R^{2a}$ is selected from the group consisting of H and $C_1$-$C_6$ alkyl.

Isomers of 3,7-dimethylocta-2,6-dienal include (E)-3,7-dimethylocta-2,6-dienal (also referred to as geranial) and (Z)-3,7-dimethylocta-2,6-dienal (also referred to as neral). Reactions in accordance with the present disclosure may be conducted with either isomer or a combination thereof; mixtures of geranial and neral are referred to as "citral" and/or "E,Z-citral" and are commercially available from a number of suppliers. Accordingly, the 3,7-dimethylocta-2,6-dienal in some embodiments contains neral, geranial, or a combination thereof. In some embodiments, the 3,7-dimethylocta-2,6-dienal is E,Z-citral.

The methods provided here can be employed using olivetol (a compound of Formula II, wherein $R^1$ is n-pentyl and $R^2$ is H), olivetolic acid (a compound of Formula II, wherein $R^1$ is n-pentyl and $R^2$ is —COOH), and analogs thereof (compounds of Formula II, wherein $R^2$ is H or —$COOR^{2a}$, and wherein $R^1$ is $C_1$-$C_4$ alkyl, branched $C_5$ alkyl, $C_6$-$C_{20}$ alkyl, $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, or $C_2$-$C_{20}$ alkenyl) for the preparation of cannabichromene, cannabichromenic acid, and analogs thereof. Olivetol, olivetolic acid, and analogs thereof may be prepared as described, for example, in International Pat. Appl. Pub. Nos. WO 2018/209143, WO 2020/092823, and WO 2020/102430, which are incorporated herein by reference in their entirety. In some embodiments, $R^2$ in the compound of Formula I and Formula II is H. In some embodiments, $R^2$ in the compound of Formula I and Formula II is —COOH. In some embodiments, $R^1$ in the compound of Formula I and Formula II is n-pentyl. In some embodiments, $R^1$ in the compound of Formula I and Formula II is methyl.

In some embodiments, the compound of Formula II is purified or semi-purified. Alternatively, the compound of Formula II (e.g., olivetol) may be used as a crude mixture (e.g., a lysate of yeast cells used for expression of olivetol).

In some embodiments, the reaction mixture contains a solvent. In some embodiments, the solvent is selected from the group consisting of toluene, chloroform, methylene chloride, dichloroethane, ethyl acetate, acetonitrile, acetone, tetrahydrofuran, benzene, ethylbenzene, xylenes, diethyl ether, dimethyl formamide, dimethyl sulfoxide, petroleum ether, and mixtures thereof. In some embodiments, the solvent is toluene, chloroform, isopropanol, or a mixture thereof. In some embodiments, the solvent is isopropanol.

In some embodiments, the diamine is selected from the group consisting of N,N'-dimethylethylenediamine; N,N-dimethylethylenediamine; N,N-diethylethylenediamine; N,N'-diphenylethylenediamine; N,N'-dibenzylethylenediamine; N,N'-bis(2-hydroxyethyl)ethylenediamine; N,N'-dimethylpropylenediamine; N,N-dimethylpropylenediamine; N,N-diethylpropylenediamine; N,N'-diphenylpropylenediamine; N,N'-dibenzylpropylenediamine; N,N'-bis(2-hydroxyethyl)propylenediamine; 1,2-diaminocyclohexane; N,N'-dimethyl-1,2-diaminocyclohexane; and 1,2-cyclopentanediamine.

In general, the reaction mixture will contain the 3,7-dimethylocta-2,6-dienal (also referred to herein as "dienal") in an amount ranging from about 0.01 molar equivalents to about 10 molar equivalents with respect to the compound of Formula II (e.g., olivetol) and/or with respect to the diamine. The reaction mixture may contain, for example, from about 0.08 molar equivalents to about 1.8 molar equivalents of the dienal, or from about 1.0 molar equivalents to about 1.5 molar equivalents of the dienal, or from about 1.05 molar equivalents to about 1.45 molar equivalents of the dienal, or from about 1.1 molar equivalents to about 1.4 molar equivalents of the dienal with respect to the compound of Formula II. The reaction mixture may contain about 0.01, 0.05, 1.0, 1.1, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.45, 1.5, 1.6, 1.7, 1.8, 1.9, or 2.0 molar equivalents of the dienal. In some embodiments, the reaction mixture contains about 1.1-10 molar equivalents of the dienal (e.g., E,Z-citral) with respect to the compound of Formula II (e.g., olivetol). In some embodiments, the reaction mixture contains about 1.1-2 molar equivalents of the dienal (e.g., E,Z-citral) with respect to the compound of Formula II (e.g., olivetol).

The reaction mixture will typically contain the diamine (e.g., N,N'-dimethylethylene-diamine) in an amount ranging from about 0.01 molar equivalents to about 10 molar equivalents with respect to the compound of Formula II (e.g., olivetol) and/or with respect to the dienal (e.g., E,Z-citral). The reaction mixture may contain, for example, from about 0.05 molar equivalents to about 1 molar equivalents of the diamine, or from about 0.1 molar equivalents to about 0.5 molar equivalents of the diamine, or from about 0.15 molar equivalents to about 0.4 molar equivalents of the diamine, or from about 0.2 molar equivalents to about 0.3 molar equivalents of the diamine with respect to the compound of Formula II. The reaction mixture may contain about 0.05, 0.1, 0.15, 0.2, 0.21, 0.22, 0.23, 0.24, 0.25, 0.26, 0.27, 0.28, 0.29, 0.3, 0.35, 0.4, 0.45, or 0.5 molar equivalents of the diamine. In some embodiments, the reaction mixture contains about 0.01-10 molar equivalents of the diamine (e.g., N,N'-dimethylethylenediamine) with respect to the compound of Formula II (e.g., olivetol). In some embodiments, the reaction mixture contains about 0.25 molar equivalents of the diamine (e.g., N,N'-dimethylethylene-diamine) with respect to the compound of Formula II (e.g., olivetol).

The reaction can be conducted at any suitable temperature. Typically, the reaction is conducted at temperatures ranging from about 20° C. to about 200° C., e.g., from about 20° C. to about 100° C., or from about 20° C. to about 80° C., or from about 20° C. to about 70° C. The conversion step is conducted for a period of time sufficient to convert the compound of Formula II to the compound of Formula I. Depending on factors such as the particular starting material, the particular diamine, and the particular solvent, the conversion time will range from a few minutes to a few hours, or longer. In some embodiments, the reaction mixture is maintained at a reaction temperature ranging from about 20° C. to about 100° C. (e.g., about 25° C., or about 30° C., or about or about 35° C., or about 40° C., or about 45° C., or about 50° C., or about 55° C., or about 60° C., or about 65° C., or about 70° C., or about 75° C., or about 80° C.). In some embodiments, the reaction mixture is maintained at the reaction temperature (e.g., about 60° C.) for a period of time ranging from about 30 minutes to about 24 hours (e.g., from about 60 minutes to about 90 minutes). Unexpectedly, long reaction times in certain instances have been found to result in degradation of desired cannabinoid products. It has been discovered, however, that short reaction times (e.g., not longer than 24 hours, or not longer than 12 hours, or not longer than 5 hours, or not longer than 3 hours) can be advantageous for preventing unwanted degradation. Reactions may be conducted under ambient atmosphere, or under an inert atmosphere (e.g., argon, nitrogen, or the like).

In some embodiments, the methods further include converting the cannabichromene-type compound of Formula I to a cannabinol-type compound of Formula III:

(III)

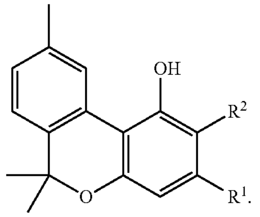

Caprioglio et al. (*Organic Letters,* 2019, 21(15): 6122-6125) have recently reported that a one-pot synthesis of CBN is possible using olivetol, citral, and an amine catalyst prior to an iodine-mediated oxidation step. However, this procedure requires an intermediate step to remove the amine catalyst, which was reported to interfere with the next oxidative step involving iodine. Provided herein is a true one-pot procedure, which does not require removal of the amine catalyst and does not use DEA controlled iodine. Rather, the process of the present disclosure employs an iodine source such as NaI and a green oxidant such as oxone which proceeds cleanly to cannabinol (CBN).

In some embodiments, the converting comprises combining the compound of Formula I with an iodine source and an oxidizing agent. Suitable iodine sources include, but are not limited to, sodium iodide, lithium iodide, potassium iodide, magnesium iodide, calcium iodide, ammonium iodide, aluminum iodide, zinc iodide, barium iodide, cesium iodide, N-iodosuccinimide, and combinations thereof. Examples of suitable oxidizing agents include, but are not limited to, potassium peroxymonosulfate, a peroxide, 2-iodoxybenzoic acid, sodium hypochlorite, and combinations thereof. In some embodiments, the iodine source is sodium iodide and the oxidizing agent is potassium peroxymonosulfate (also referred to as OXONE®).

The reaction mixture will typically contain the iodine source (e.g., sodium iodide) and/or the oxidizing agent (e.g., potassium peroxymonosulfate) in an amount ranging from about 1 molar equivalent to about 10 molar equivalents with respect to the compound of Formula II (e.g., olivetol) and/or the compound of Formula I (e.g., cannabichromene). The reaction mixture may contain, for example, from about 1 molar equivalents to about 5 molar equivalents of the iodine source and/or oxidizing agent, or from about 1 molar equivalents to about 3 molar equivalents of the iodine source and/or oxidizing agent, or from about 1.25 molar equivalents to about 2.75 molar equivalents of the iodine source and/or oxidizing agent, or from about 1.5 molar equivalents to about 2.5 molar equivalents of the iodine source and/or oxidizing agent, or from about 1.8 molar equivalents to about 2.2 molar equivalents of the iodine source and/or oxidizing agent with respect to the compound of Formula II or Formula I. The reaction mixture may contain about 1, 1.1, 1.2, 1.3, 1.4, 1.5, 1.6, 1.7, 1.8, 1.9, 2, 2.1, 2.2, 2.3, 2.4, or 2.5 molar equivalents of the iodine source and/or oxidizing agent. In some embodiments, the reaction mixture contains about 1.8-2.2 molar equivalents of the iodine source (e.g., sodium iodide) and 1.8-2.2 molar equivalents of the oxidizing agent (e.g., potassium peroxymonosulfate) with respect to the compound of Formula II (e.g., olivetol). Typically, reactions for forming the compound of Formula III will be conducted at temperatures ranging from about 20° C. to about 200° C. (e.g., from about 20° C. to about 180° C., or from about 90° C. to about 140° C., or from about 100° C. to about 120° C.) for a period of time ranging from about 30 minutes to about 24 hours (e.g., from about 60 minutes to about 90 minutes, or from about 60 minutes to about 3.5 hours). Advantageously, the step of converting the compound of Formula I to a compound of Formula III can be conducted as a one-pot reaction in the reaction mixture. The iodine source and/or the oxidizing agent may be added to the reaction mixture in one or more portions without isolating the compound of Formula I (e.g., cannabichromene), and other reaction conditions (e.g., reaction temperature, quantity of solvent) may be adjusted to promote formation of the compound of Formula III (e.g., cannabinol).

In some embodiments, an acid may be used with a diamine to convert CBC or an analog thereof (as an intermediate or as a starting material) to mixed intermediates that are then aromatized to CBN or an analog thereof using iodine or metal catalysts as described above.

Examples of suitable acids include, but are not limited to, Brønsted acids such as mineral acids (e.g., hydrochloride acid, sulfuric acid, nitric acid, or the like), sulfonic acids (e.g., p-toluenesulfonic acid, trifluoromethanesulfonic acid, and the like), and carboxylic acids (e.g., trifluoroacetic acid and the like), as well as Lewis acids such as copper (I) chloride and boron trifluoride. In some embodiments, the acid is p-toluenesulfonic acid. The reaction mixture may contain, for example, from about 0.1 molar equivalents to about 1.1 molar equivalents of the acid, or from about 0.5 molar equivalents to about 1 molar equivalents of the acid, or from about 0.7 molar equivalents to about 0.8 molar equivalents of the acid with respect to the diamine. The reaction mixture may contain about 0.55, 0.6, 0.65, 0.7, 0.71, 0.72, 0.73, 0.74, 0.75, 0.76, 0.77, 0.78, 0.79, 0.8, 0.85, 0.9, or 0.95 molar equivalents of the acid. In some embodiments, the reaction mixture contains about 0.01-10 molar equivalents of the diamine (e.g., N,N'-dimethylethylenediamine) with respect to the acid (e.g., p-toluenesulfonic acid). In some embodiments, the reaction mixture contains about 1.0 molar equivalent of the diamine (e.g., N,N'-dimethylethylene-diamine) with respect to the acid (e.g., p-toluenesulfonic acid).

Other reagents may also be used for forming compounds of Formula III, in addition to the combination of iodine source and oxidizing agent described above. In some embodiments, the reaction is conducted with an oxidizing agent as described above (e.g., potassium peroxymonosulfate, a peroxide, 2-iodoxybenzoic acid, or sodium hypochlorite) without an iodine source. In some embodiments, the reaction is conducted with elemental sulfur. In some embodiments, the reaction is conducted with a metal dehydrogenation catalyst. Examples of suitable catalysts include, but are not limited to, palladium phosphine complexes; a supported metal catalyst such as palladium on carbon, palladium hydroxide on carbon, platinum on carbon, palladium on alumina, or platinum on alumina; platinum dioxide; iridium catalysts; rhodium catalysts; Raney nickel; tetra-n-butylammonium decatungstate (TBADT); cobaloxime pyridine chloride (COPC); aerobic palladium catalysts such as $Pd(OAc)_2/Cu(II)$ for use with $O_2$; and allyl-palladium catalysts such as $Pd(OAc)_2/NaCO_3/$(allyl diethyl phosphate). In some embodiments, the metal dehydrogenation catalyst comprises palladium on carbon, platinum on carbon, palladium on alumina, platinum on alumina, or a combination thereof. Loading of the catalyst on the support will typically range from about 5% by weight to about 20% by weight. The catalysts may be added in "wet" form (e.g., containing 50% water by weight) or dry form.

Reaction mixtures may contain, for example, from about 0.01 molar equivalents to about 0.5 molar equivalents of the catalyst, or from about 0.05 molar equivalents to about 0.25 molar equivalents of the catalyst, or from about 0.05 molar equivalents to about 0.1 molar equivalents of the catalyst with respect to the compound of Formula I. The reaction mixture may contain about 0.05, 0.06, 0.07, 0.08, 0.09, 0.1 molar equivalents of the catalyst. In some embodiments, the reaction mixture contains about 0.01-0.1 molar equivalents of the catalyst (e.g., 10% Pd/carbon, wet or dry) and about 0.5-1.1 molar equivalents acid (e.g., p-toluenesulfonic acid) with respect to the compound of Formula II. Reaction times and temperatures may be varied as described above. For example, the reaction may be conducted at temperatures ranging from about 20° C. to about 200° C. for periods of time ranging from about 1 hour to about 12 hours (e.g., at about 110-125° C. for about 6-10 hr, under ambient atmosphere or an inert atmosphere).

III. EXAMPLES

Example 1. Preparation of Cannabichromene

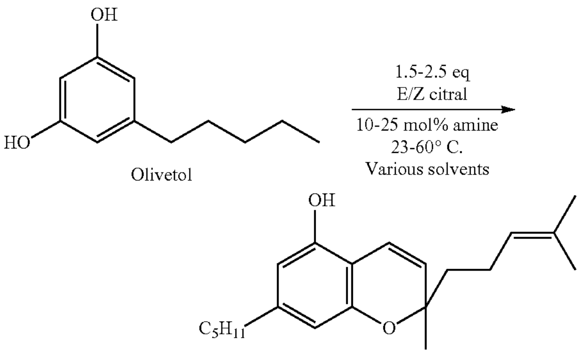

Olivetol

Cannabichromene (CBC)

To 0.9 mL of toluene (0.22 M) was added 36 mg (0.2 mmol) of olivetol followed by 0.038 mL of E,Z-citral (1.15 eq). A 5-μL aliquot of the reaction mixture was diluted into 995 μL of 95% EtOH, and 10 μL of this solution was injected into a Waters 2695 HPLC equipped with a DAD detector monitoring at 230 nm to establish a starting area baseline for olivetol. The reaction was initiated by addition of 5.5 μL (0.25 eq) of dimethylethylethyenediamine (DMEAD) and subsequent samples were prepared and analyzed by HPLC. Yield was calculated based on peak area, using the extinction coefficient ratio for olivetol/cannabichromene (CBC) of 5.6 at 230 nm, established with a CBC standard (1 mg/mL, obtained from Cerilliant). The reaction was monitored by HPLC for yield at different time points as summarized in Table 1.

TABLE 1

| Conditions | | Molar |
|---|---|---|
| Time | Temp | Yield of CBC |
| 30 min | 23° C. | 34% |
| 30 min | 60° C. | 71% |
| 60 min | 60° C. | 78% |
| 90 min | 60° C. | 89% |
| 120 min | 60° C. | 80% |

Table 2 shows the effect of solvent, reaction time and temperature, and amine catalyst (DMEAD vs mono-amines) at different reaction time points: (E,Z-citral=1.15 equivalents).

TABLE 2

| Conditions | | | Molar Yield of Cannabichromene (CBC) | | | | |
|---|---|---|---|---|---|---|---|
| Time | Temp | Solvent | DMEDA | IPA | IPM | BA | IPN |
| 30 min | 23° C. | $CHCl_3$ | 40% | 6% | 0.2% | 9% | 12% |
| 23 h | 23° C. | $CHCl_3$ | 72% | 82% | 3% | 73% | 73% |
| 1 h | 60° C. | toluene | 95% | 48% | 3% | 76% | 52% |
| 23 h | 60° C. | toluene | 79% | 72% | 7% | 52% | 71% |
| 45 min | 60° C. | isopropanol | 7% | 0% | 0% | 0% | 0% |
| 24 h | 60° C. | isopropanol | 73% | 1.3% | 1.4% | 2.0% | 1.4% |
| 44 h | 60° C. | isopropanol | 69% | 1.8% | 1.7% | 2.0% | 3.1% |

E,Z-Citral = 1.15 eq, solvent concentration = 0.22M, Amine catalyst = 0.25 eq
Yield based on extinction coefficient ratio of CBC/olivetol = 5.6 at 230 nm
DEMEAD = dimethylethylenediamine, IPA = isopropylamine, IPM = N-isopropyl-N-methylamine, BA = n-butylamine, IPN = i-pentylamine Chlorinated solvents generally resulted in faster reactions, especially when employing DMEDA. Toluene required higher temperature but shorter reaction times for DMEDA. DMEDA was the only catalyst to give a substantial yield under the initial test conditions, providing significantly higher yields than mono-amines. Yields with DMEDA drop with extended heating times, and increased impurities were also observed.

Table 3 shows the effect of solvent, reaction time and temperature, and amine catalyst after different reaction time points.

TABLE 3

| Conditions | | | Yield of Cannabichromene (CBC) | | | | |
|---|---|---|---|---|---|---|---|
| Time | Temp | Solvent | DMEDA | ED | DAC | DP | TB |
| 1 h | 23° C. | toluene | 42% | 7.7% | 17% | 5.3% | 0.4% |
| 30 min | 60° C. | toluene | 52% | 28% | 32% | 25% | — |
| 90 min | 60° C. | toluene | 75% | 67% | 70% | 61% | 16% |
| 23 h | 60° C. | toluene | 92% | 81% | 85% | 65% | 73% |
| 3 days | 60° C. | toluene | 87% | 80% | 82% | 72% | 83% |

E,Z-Citral = 1.35 eq, solvent concentration = 0.22M, Amine catalyst = 0.25 eq
Yield based on extinction coefficient ratio of CBC/olivetol = 5.6 at 230 nm
DEMEDA = dimethylethylenediamine, ED = ethylenediamine, DAC = 1,2-diaminocyclohexane, DP = diaminopropane, TB = t-butylamine The DMEDA catalyst proved to be unexpectedly faster than ethylene diamine (ED). DMEDA provided a higher yield at extended times at 60° C. Other diamines such as DAC and DP also catalyzed the reaction. A drop in yield at longer reaction times indicates that the product may be sensitive to equivalents of citral used (e.g., 1.35 eq vs 1.15 eq, compare with Table 2).

Final purified color characteristics related to minor impurities are important to the finished distilled products and their acceptability for pharmaceutical-grade compositions.

CBC, when fully purified by preparative chromatography, is a clear oil. Notably, the DMEDA catalyst provided reaction mixtures with a light yellow color whereas the IPA catalyst resulted in reaction mixtures having a deep red color that was carried through into the final distilled oil as an orange to orange-red color.

Example 2. Preparation of Cannabinol

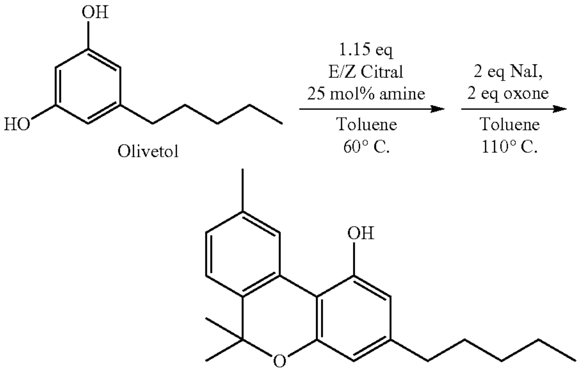

Olivetol

Cannabinol (CBN)

To 9 mL of toluene (0.22M) was added 360 mg (2 mmol) of olivetol followed by 0.38 mL of E,Z-citral (1.15 eq) which was heated at 60° C. for 2 hours. To this solution was further added 2.4 eq (740 mg) of NaI followed by 2.1 eq (1.45 g) of oxone and heated to 110° C. for 3 hours. The reaction was cooled and filtered through a 5 μm filter and concentrated in vacuo to give 660 mg of a dark viscous oil. HPLC analysis indicated that all of the CBC was consumed and the resulting CBN product was identical to a CBN standard (obtained from Cerilliant, 1 mg/mL).

An acid may also be used to promote formation of cyclized intermediates for conversion to cannabinol. To 0.9 mL of toluene (0.22M) is added 36.0 mg (2 mmol) of olivetol followed by 0.038 mL of E,Z-citral (1.15 eq). The reaction is initiated by addition of 55 μL (0.25 eq) of DMEAD and the solution is heated for 2 hours at 110° C. To the reaction is added 0.75 equivalents of p-toluenesulfonic acid (3×0.25 eq) to protonate the diamine, and heating is continued for about 2 hours. NaI/oxone or 12 is added, or the reaction mixture is subjected to dehydrogenation conditions to yield CBN after 3-4 hours at 110° C. The reaction is cooled and filtered through a 5-μm filter and concentrated in vacuo to provide the CBN as a viscous oil which is identical to a CBN standard (obtained from Cerilliant, 1 mg/mL) by HPLC analysis.

Example 3. Preparation of Cannabinol by Acid Catalyzed Dehydrogenation and Metal-Catalyzed Cyclization of In Situ Prepared Cannabichromene Olivetol (288 mg; 1.6 mmol) was treated with citral (302 μL; 2.0 mmol) and DMEAD (44 μL; 0.25 eq) dissolved in 8 mL xylene (0.2 M), and heated for 2 h at 60° C. The reaction mixture was then divided into 500-μL aliquots for use in the reactions summarized in Table 4. The reactions in Table 4 were conducted with 10 mg of TsOH (1 eq) and 5 mg of the metal catalysts (A, B, C, D, E, or F). The reactions were heated to 110° C. and monitored by HPLC at different time points as shown in Table 4. Reaction yields of cannabinol were calculated relative to a maximum yield demonstrated by catalyst B at 48 h.

TABLE 4

| Reaction Time | Relative Yield of Cannabinol (CBN) Metal Catalysts* | | | | | |
|---|---|---|---|---|---|---|
| (at 110 °C. in toluene) | A | B | C | D | E | F |
| 24 h | 49% | 40% | 10% | 7% | 0% | 14% |
| 48 h | 76% | 100% | 13% | 26% | 18% | 57% |
| 3 days | 43% | 71% | 12% | 20% | 66% | 56% |
| 4 days | 40% | 41% | 17% | 24% | 40% | 36% |

*A = 10% Pd/carbon/wet; B = 5% $Pd(OH)_2$/carbon; C = 20% $Pd(OH)_2$/carbon/50% water; D = 10% Pt/carbon; E = $PtO_2$; F = $PtO_2$•$H2O_x$

Example 4. Preparation of CBN Analog 3,6,6,9-Tetramethyl-6H-Benzo[c] Chromen-1-ol

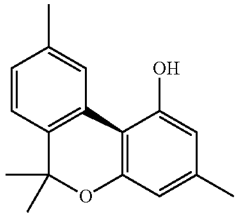

To a solution of 5-methyl-benzene-1,3-diol (orcinol; 99 mg; 0.8 mmol) in 1.8 mL of toluene was added citral (152 μL, 1.2 eq) followed by DMEAD (22 μL; 0.25 eq) to initiate the reaction. The reaction was stirred for 21 h, heated for 30 min at 60° C., cooled, and loaded onto a preparative C-18 column eluting with a gradient of 0% →100% acetonitrile/water/0.1% formic acid to provide 43 mg (21%) of 2,7-dimethyl-2-(4-methyl-pent-3-enyl)-2H-chromen-5-ol as an oil. The resulting intermediate was treated with 1 eq of TsOH and catalyst A (10% Pd/carbon/wet) in toluene and heated for 8 h at 120° C. The solution was cooled and purified on C-18 followed by preparative plate TLC eluted with 10% EtOAc to afford 5.5 mg of 3,6,6,9-Tetramethyl-6H-benzo[c]chromen-1-ol. 99% by HPLC: Calcd $C_{17}H_{18}O_2$ 254.13, LC-MS/ESI Found: M+H: 255.10; $^1$H-NMR ($CDCL_3$, 300 MHz): δ 1.63 (6H, s), 2.26 (3H, s), 2.38 (3H, s), 5.23 (1H, s), 6.29 (1H, s), 6.42 (1H, s), 7.075 (AB, 1H, J=9), 7.145 (AB, 1H, J=9), 8.16 (1H, s). This reaction sequence was found to be particularly useful for obtaining high-purity cannabinoid analogs (e.g., ≥99% pure) that are acceptable for pharmaceutical-grade compositions.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for preparing a compound according to Formula I:

(I)

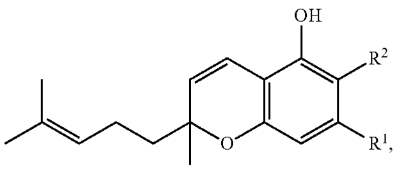

or a salt thereof, the method comprising:

forming a reaction mixture comprising 3,7-dimethylocta-2,6-dienal, a diamine, and a compound of Formula II:

(II)

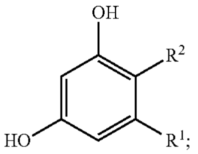

and maintaining the reaction mixture under conditions sufficient to form the compound of Formula I; wherein:

$R^1$ is selected from the group consisting of $C_1$-$C_{20}$ alkyl, $C_1$-$C_{20}$ haloalkyl, $C_1$-$C_{20}$ hydroxyalkyl, deuterated $C_1$-$C_{20}$ alkyl, tritiated $C_1$-$C_{20}$ alkyl, and $C_2$-$C_{20}$ alkenyl;

$R^2$ is selected from the group consisting of H and —$COOR^{2a}$; and $R^{2a}$ is selected from the group consisting of H and $C_1$-$C_6$ alkyl.

2. The method of claim 1, wherein the diamine is selected from the group consisting of N,N'-dimethylethylenediamine; N,N-dimethylethylenediamine; N,N-diethylethylenediamine; N,N'-diphenylethylenediamine; N,N'-dibenzylethylenediamine; N,N'-bis(2-hydroxyethyl)ethylenediamine; N,N'-dimethylpropylenediamine; N,N-dimethylpropylenediamine; N,N-diethylpropylenediamine; N,N'-diphenylpropylenediamine; N,N'-dibenzylpropylenediamine; N,N'-bis(2-hydroxyethyl)propylenediamine; 1,2-diaminocyclohexane; N,N'-dimethyl-1,2-diaminocyclohexane; and 1,2-cyclopentanediamine.

3. The method of claim 1, wherein the reaction mixture contains about 1.1-10 molar equivalents of the 3,7-dimethylocta-2,6-dienal with respect to the compound of Formula II.

4. The method of claim 3, wherein the reaction mixture containing about 1.1-2 molar equivalents of the 3,7-dimethylocta-2,6-dienal with respect to the compound of Formula II.

5. The method of any claim 1, wherein the reaction mixture contains about 0.01-10 molar equivalents of the diamine with respect to the compound of Formula II.

6. The method of claim 5, wherein the reaction mixture contains about 0.25 molar equivalents of the diamine with respect to the compound of Formula II.

7. The method of claim 1, wherein the reaction mixture is maintained at a reaction temperature ranging from about 20° C. to about 70° C.

8. The method of claim 7, wherein the reaction mixture is maintained at the reaction temperature for a period of time ranging from about 30 minutes to about 24 hours.

9. The method of claim 1, wherein the reaction mixture further comprises a solvent.

10. The method of claim 9, wherein the solvent is selected from the group consisting of toluene, chloroform, methylene chloride, dichloroethane, ethyl acetate, acetonitrile, acetone, tetrahydrofuran, benzene, ethylbenzene, xylenes, diethyl ether, dimethyl formamide, dimethyl sulfoxide, petroleum ether, and mixtures thereof.

11. The method of claim 9, wherein the solvent is selected from the group consisting of toluene, chloroform, isopropanol, and mixtures thereof.

12. The method of claim 1, wherein the 3,7-dimethylocta-2,6-dienal comprises neral, geranial, or a combination thereof.

13. The method of claim 1, wherein the 3,7-dimethylocta-2,6-dienal comprises E,Z-citral.

14. The method of claim 1, wherein $R^2$ is H.

15. The method of claim 1, wherein $R^2$ is —COOH.

16. The method of claim 1, wherein $R^1$ is n-pentyl.

17. The method of claim 1, wherein the compound of Formula II is purified or semi-purified.

18. The method of claim 1, further comprising converting the compound of Formula I to a compound of Formula III:

(III)

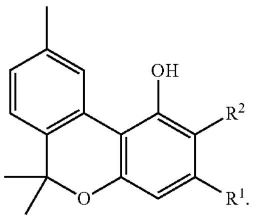

19. The method of claim 18, wherein the converting comprises combining the compound of Formula I with an iodine source and an oxidizing agent.

20. The method of claim 19, wherein the iodine source is selected from the group consisting of sodium iodide, lithium iodide, potassium iodide, magnesium iodide, calcium iodide, ammonium iodide, aluminum iodide, zinc iodide, barium iodide, cesium iodide, N-iodosuccinimide, and combinations thereof.

21. The method of claim 18, wherein the converting comprises combining the compound of Formula I with an oxidizing agent.

22. The method of claim 19, wherein the oxidizing agent is selected from the group consisting of potassium peroxymonosulfate, a peroxide, 2-iodoxybenzoic acid, sodium hypochlorite, and combinations thereof.

23. The method of claim 18, wherein the converting comprises combining the compound of Formula I with sodium iodide and potassium peroxymonosulfate.

24. The method of claim 18, wherein the converting comprises combining the compound of Formula I with elemental sulfur.

25. The method of claim 18, wherein the converting comprises combining the compound of Formula I with a metal dehydrogenation catalyst.

26. The method of claim 25, wherein the metal dehydrogenation catalyst comprises palladium on carbon, palladium hydroxide on carbon, platinum on carbon, platinum dioxide, palladium on alumina, or platinum on alumina.

27. The method of claim 18, wherein the converting further comprises combining the compound of Formula I with an acid.

28. The method of claim 27, wherein the acid is p-toluenesulfonic acid.

29. The method of claim 18, wherein the step of converting the compound of Formula I to a compound of Formula III is conducted as a one-pot reaction in the reaction mixture for forming the compound of Formula I.

30. The method of claim 1, wherein the compound of Formula I is

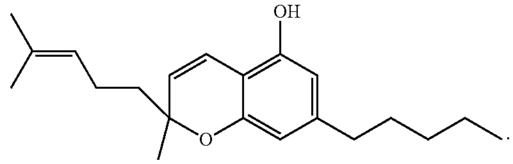 [SMILES: CCCCCc1cc(O)c2c(c1)OC(C)(CCC=C(C)C)C=C2]

31. The method of claim 18, wherein the compound of Formula III is

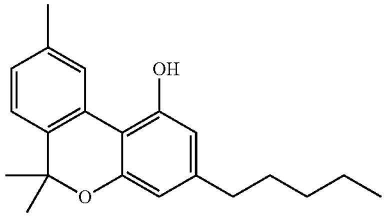

or

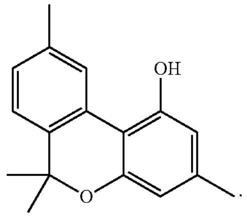

* * * * *